United States Patent [19]

Bombardelli et al.

[11] Patent Number: 5,104,655
[45] Date of Patent: Apr. 14, 1992

[54] POLYUNSATURATED ACIDS HAVING VASOKINETIC ACTION AND PHARMACEUTICAL AND COSMETIC FORMULATIONS CONTAINING THEM

[75] Inventors: Ezio Bombardelli; Sergio B. Curri, both of Milan, Italy

[73] Assignee: Indena S.p.A., Milan, Italy

[21] Appl. No.: 670,349

[22] Filed: Mar. 15, 1991

Related U.S. Application Data

[63] Continuation of Ser. No. 224,870, Jul. 26, 1988, abandoned.

[30] Foreign Application Priority Data

Jul. 27, 1987 [IT] Italy .............................. 21453 A/87

[51] Int. Cl.$^5$ .................... A61K 35/78; A61K 31/685
[52] U.S. Cl. ................................. 424/195.1; 514/78; 514/552; 514/558; 514/826; 514/846; 514/861

[58] Field of Search ................ 514/78, 552, 558, 826, 514/846, 861; 424/195.1

[56] References Cited

U.S. PATENT DOCUMENTS

| | | | |
|---|---|---|---|
| 4,358,442 | 11/1982 | Wirtz-Peitz et al. | 514/76 |
| 4,444,755 | 4/1984 | Horrobin | 424/642 |
| 4,508,703 | 4/1985 | Redziniak et al. | 424/450 |
| 4,681,896 | 7/1987 | Horrobin | 514/552 |

*Primary Examiner*—John W. Rollins
*Attorney, Agent, or Firm*—Bucknam and Archer

[57] ABSTRACT

Some polyunsaturated acids (ximeninic acid, γ-homolinolenic acid, eicosapentaenoic acid), suitably formulated and administered by the topical route, possibly in form of glicerids or of complexes with phospholipids, have vasokinetic and vasodilative properties.

3 Claims, No Drawings

POLYUNSATURATED ACIDS HAVING VASOKINETIC ACTION AND PHARMACEUTICAL AND COSMETIC FORMULATIONS CONTAINING THEM

This is a continuation of application Ser. No. 224,870, filed July 26, 1988, ABN.

The present invention relates to pharmaceutical and cosmetic compositions for topical administration, containing polyunsaturated fatty acids, possibly in form of mono-, di- or triglicerids or of complexes with natural or synthetic phospholipids.

The polyunsaturated acids being the active ingredients of the compositions provided by the invention comprise ximenic or ximeninic acid, γ-homo-linolenic acid, docosahexaenoic acid, eicosapentaenoic acid and eicosahexaenoic acid.

Ximenic or ximeninic acid is contained in a number of vegetal species such as *Ximenia african, Santalum album*, etc., whereas the three other acids are well-known to be present in different animals or vegetables, among which the more important plants are *Enothera biennis, Borago officinalis*, etc.

Eicosapentaenoic and docosahexaenoic acids, which are contained in fish oil, have been known for a long time to have valuable pharmacological properties such as antithrombotic and antiarteriosclerotic activities, upon oral or dietary administrations.

Now, it has surprisingly been found that said polyunsaturated acids, when topically administered, cause such beneficial vasokinetic and vasodilative effects as to increase sphygmic activity and blood stream in arteries and precapillary arterioles as well as in capillaries and venules associated.

Therefore, the compositions of the invention are used in a variety of conditions requiring an improvement in cutis trophism and in superficial and deep microcirculation of cutis itself or of other tissues or organs.

Particularly, the compositions of the invention proved to be useful in the pharmaceutical field, for the topical epicutaneous treatment of functional or organic peripheral vasculopathies, and, in the cosmetic field, for the treatment and the prophylaxies of hair fall due both to natural causes (androgenetic alopecia) and pathologic causes, and also for the treatment of sexual impotence.

For the intended uses, particularly suited forms are therefore creams, ointments, lotions, gels, etc., prepared by means of conventional methods and excipients, such as those described in "Remington's Pharmaceutical Sciences Handbook", Hack Pub. Co., N.Y., USA.

Polyunsaturated fatty acids being the active ingredients can be used in the pure state or in form of salts or of extracts containing them, possibly esterified with glycerol.

According to a particularly preferred aspect of the invention, complexes of said acids with natural or synthetic phospholipids are used, which provide a further object of the invention and can be represented by the following formula:

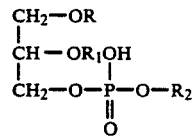

in which: R and $R_1$, which can be the same or different, mainly represent acyl residues of palmitic, stearic, oleic, linoleic and linolenic acids, whereas $R_2$ is a choline, ethanolamine or serine residue.

For the cosmetic application, particularly preferred is the use of vegetable or natural phospholipids, such as those from soy or from bovine or porcine cutis, liver or brain, which are similar to those present in human derma; for other applications the use of a chemically homogeneous phospholipid, defined in the structural units thereof (acyl and phosphorylamino groups), is preferred.

Such complexes are prepared by reacting the unsaturated fatty acid or an oil or extract containing it in an aprotic solvent with the phospholipid dissolved in the same solvent. Phospholipid/fatty acid molar ratios range from 0.5 to 2, more preferably about 1. After complete dissolution, complexes are recovered by removing the solvent under vacuum, by lyophilization or precipitation with non-solvents.

The obtained complexes are lipophilic, completely soluble in apolar solvents and, when treated with water, give micellar microdispersions maintaining a lipophilic character. Formation of the complex is confirmed by NMR analysis, from which the polar head of phospholipid seems to be mainly involved in the formation of the complex.

As a matter of fact, in case of phospholipids with saturated acyl residues, $^1$H-NMR signals characteristic of hydrogen atoms are no more detectable and a broading in the band, due to the -N(Me)$_3$ group, is noted; in $^{13}$C-NMR spectrum the signals of carbon atoms of the complexed acid undergo such marked changes as the ones of cholinic or glyceric residues, whereas in -P-NMR spectrum a broading in phosphorous band is evidenced in comparison with the spectrum of the uncomplexed phospholipid.

Phospholipid complexes of fatty acids show advantages in terms of bioavailability and activity by the topical route and can also be conveniently obtained directly from vegetable extracts or from oils containing the above cited fatty acids.

Said complexes can be used either alone, microdispersed in water, in which they form micellar lipophilic aggregates, or diluted in oils conventionally used in pharmaceutical and cosmetic formulations, or they can be included together with other acids or compatible active ingredients, in the different oil/water emulsions and viceversa, etc.

In formulations for both pharmaceutical and cosmetic use, dosages considered biologically active are vary variable, and are generally comprised in concentrations from 0.1% to about 10%.

Some results obtained by topical administration in man of pure ximeninic acid and of the triglycerid thereof, in comparison with a placebo (olive oil) are summarized in Table 1.

The results obtained with pure ximeninic acid complexed with soy phospholipids are summarized in Table II, said results being instrumentally determined using thermographic and plethysmographic methods according to the reported procedures. High resolution liquid crystal contact thermography was used, which can detect changes of ±0.3°–0.5° C. in cutaneous temperature and therefore is suited to the study of functional changes in cutaneous microcirculation. To such a method, infra-red plethysmography (i.r. Photo-Pulse Plethysmography), was associated, by which the entity of vasomotility (sphygmic+vasomotion activities) fo small arteries and arterioles of subpapillary plexus in even very restricted cutis areas, can be qualititatively and quantitatively determined. In practice the following method was used: under basal conditions, a HPCT of temporo-zygomatic area and of the cheek, or of superolateral area of the thigh, was performed; then epicutaneous application of the test substance (application of 10 g of oil or extract on a 10×10 cm cutis area) was carried out.

Subsequent readings were effected at regular time intervals (0 t=15=30=45=60 or more minutes).

Simoultaneously, the reading head of the plethysmograph was applied to a well delimited cutis area of the same body areas and readings of the plot were performed at the same time intervals.

Ximenia africana and of ximenic acid, and of the corresponding complexes with phospholipids, are able to significantly increase vasomotion of cutaneous small arteries improving, as a consequence, rate and volume of blood stream opening capillary network that were closed before, which brings about an increase in local cutaneous temperature, that can be evaluated thermographically and thermometrically, without causing erythematous manifestations or rubeosis. The duration of the improvement in local microcirculation is by far higher than the one that can be obtained with known vasoactive drugs which are applied by cutaneous route.

Ximenic acid and other polyunsaturated fatty acids object of the invention, in their various derived forms, proved to be also useful in the epicutaneous treatment of scalp areas affected by alopecia or abnormal fall of hair due to an insufficient bloodstream in hair follicles.

The same method as in the previous test was used, but air bed HPCT was adopted, since it allows a better resolution of the thermographic map of convex surfaces, such as skull cap. On the whole, 22 subjects were treated, in whom both the increase in cutaneous temperature and the increase in arterio-arteriole sphygmic activity of Galea capitis were recorded.

TABLE 1

Cutaneous vasomotion.
Values found after the treatment

| CASE | TREATMENT | 00' | 10' | 17' | 22' | 30' | INCREASE PERCENTAGES IN COMPARISON WITH THE BASAL VALUE | | | |
|---|---|---|---|---|---|---|---|---|---|---|
| | | | | | | | % 00'-10' | % 00'-17' | % 00'-22' | % 00'-30' |
| B.V. 38 years | Olive oil | 100.70 | 102.60 | 184.40 | 158.20 | 190.20 | 1.89 | 83.12 | 57.10 | 88.88 |
| P.B. 63 years | Olive oil | 92.80 | 117.40 | 88.40 | 142.00 | 164.00 | 26.51 | 4.74 | 53.02 | 76.72 |
| MEANS | — | 96.75 | 110.00 | 136.40 | 150.10 | 177.10 | 14.20 | 39.19 | 55.06 | 82.80 |
| | | | | | | | 13.70 | 40.98 | 55.14 | 83.05 |
| D.S. 40 years | ximeninic acid* | 105.70 | 275.00 | 319.80 | 196.40 | 167.40 | 160.17 | 202.55 | 85.81 | 58.37 |
| B.V. 30 years | ximeninic acid* | 101.80 | 384.80 | 474.40 | 475.20 | 392.20 | 278.00 | 366.01 | 366.80 | 285.27 |
| P.B. 63 years | ximeninic acid* | 135.40 | 244.20 | 243.60 | 286.50 | 334.60 | 80.35 | 79.91 | 111.60 | 147.12 |
| MEANS | — | 114.30 | 301.33 | 345.93 | 319.37 | 298.07 | 172.84 | 216.16 | 188.07 | 163.59 |
| | | | | | | | 163.63 | 202.65 | 179.41 | 160.78 |

* administered as 2.5% lotion

TABLE 2 cutaneous vasomotion.
Values found after treatment with ximeninic acid complexed with
soy phosphatidylcholine (2.5% lotion).

| CASE | 00' | 10'-17' | 17'-23' | 30'-45' | 45'-60' |
|---|---|---|---|---|---|
| Nr. 1 | 75.40 | 324.50 | 470.50 | 475.20 | 414.00 |
| Nr. 2 | 95.85 | 312.40 | 368.80 | 258.00 | |
| Nr. 3 | 188.00 | 715.40 | 581.00 | | |
| Nr. 4 | 95.30 | 255.10 | 350.40 | 277.90 | |
| Nr. 5 | 208.80 | 585.50 | 628.40 | 552.40 | 486.60 |
| MEANS | 119.75 | 450.77 | 473.43 | 390.88 | 513.80 |

| Increase percentages in comparison with the basal value. | | | | |
|---|---|---|---|---|
| CASE | % 00'-17' | % 00'-23' | % 00'-45' | % 00'-60' |
| Nr. 1 | 330.37 | 524.01 | 530.24 | 449.07 |
| Nr. 2 | 225.93 | 284.77 | 169.17 | |
| Nr. 3 | 280.53 | 209.04 | | |
| Nr. 4 | 167.68 | 267.68 | 191.61 | |
| Nr. 5 | 180.41 | 200.96 | 164.56 | 133.05 |
| MEANS | 278.94 | 339.27 | 263.89 | 347.40 |
| % > MEANS | 276.42 | 295.35 | 226.41 | 329.06 |

Vasomotion of the acral extremities was performed (fingertips, ungual plica, palmar root of fingers, thenal and hypothenal eminences) in normal subjects of both sexes affected by functional or organic disturbances of cutaneous microcirculation (Raynaud disease, Sclerodermia).

On the whole, 20 subjects whose median age was 46±4.2 years were treated. The obtained results show that the epicutaneous applications of the oily extract of Therefore, this datum is superimposable to the one concerning other cutaneous areas of the body. Ximeninic acid, unsaturated acids and derivatives thereof can be therefore used in the treatment of alopecia and of related problems requiring the use of vasodilating and vasokinetic drugs of different nature to stop the fall of hair or to stimulate its growth. A further use relates to the strenghtening of hair that, when treated after the usual washing for example with the ximeninic acid/-phospholipids complex, become easier to comb and more plastic: at the same time, a reduction, sometimes very marked, of seborroic and furfuraceous components occurs. This use is particularly suited for the treatment of subjects affected by alopecia.

A further use is the topic treatment of impotentia erigendi of vascular origin. The epicutaneous application on penis causes a rapid erection of vascular kind that lasts for a satisfactory period of time.

The following examples further illustrate the invention, without limiting it.

EXAMPLE 1

Preparation of ximeninic acid triglyceride from Ximenia africana oil 50 g of an oil obtained by extraction with hexane of Ximenia africana fruits was chromatographed on a 600 g silica gel column previously stabilized with a 95:5 cyclohexane-ethyl acetate mixture and eluted with the same solvent mixture.

The fractions having intermediate polarity were collected containing a single compound which was found to be the more abundant component of the extract. After evaporating the solvent and drying the residue under vacuum at 50° C. overnight, 18 g of a pale yellow oil was obtained, having MW=872, determined by mass spectrometry, corresponding to the triglyceride of ximeninic acid.

EXAMPLE 2

Preparation of the complex of ximeninic acid with distearoyl phosphatidylcholine 2.8 g of ximeninic acid was dissolved together with 15.5 g of synthetic distearoyl phosphatidylcholine (99%) in 50 ml of anhydrous methylene chloride.

The starting suspension was heated to mild reflux to complete dissolution, solvent was removed under vacuum and the solid residue was dried at 40° C. under vacuum overnight. The obtained white solid had m.p. 120° C. and $^1$H-NMR in CDCl$_3$ with no signals of the protons on ximeninic acid double bond, said signals appearing again after addition of DMSO or of another solvent having a high dielectric power, which could cleave such a type of compounds.

EXAMPLE 3

Preparation of the complex of ximeninic acid with soy phospholipids 2.78 g of ximeninic acid was dissolved together with 15.3 g of soy phosphatidylcholine in 50 ml of anhydrous methylene chloride.

The mixture was left to stand for 2 hours, the solvent was evaporated off under vacuum at 40° C. and the product was dried at 40° C. overnight. 17 g of a yellow product was obtained, melting at 55° C.

EXAMPLE 4

Preparation of the complex of γ-homo-linolenic acid with distearoyl phosphatidylcholine 2.78 g of γ-homo-linolenic acid was dissolved together with 15.76 g of distearoyl phosphatidylcholine in 100 ml of anhydrous dioxane. The obtained solution was maintained for 2 hours at room temperature, then lyophilized. 18 g of a white powder was obtained, having the spectroscopic characteristics of a complex.

EXAMPLE 5

| Cream | |
|---|---|
| 100 g of cream contain: | |
| Ximeninic acid | 5 g |
| Isopropyl myristate | 5 g |
| Wheat germ oil | 2.5 g |
| Ethyl alcohol | 1.5 g |
| Imidazolidinylurea | 0.3 g |
| Methyl hydroxybenzoate | 0.1 g |
| Polysorbate 80 | 2 g |
| Carboxyvinylpolymer | 1 g |
| Sodium hydroxide 10% | 2 g |

| Cream -continued | |
|---|---|
| Perfumed composition (essence) | 0.1 g |
| Depurated water | 80.5 g |

EXAMPLE 6

| Gel | |
|---|---|
| 100 g of gel contain: | |
| Ximeninic acid complex | 2.5 g |
| Softigen 767 C$_8$-C$_{12}$ ethoxylated triglycerids) | 25 g |
| Volpo 20 (polyoxyethylene 20 oleylether) | 7 g |
| Imidazolidinylurea | 0.3 g |
| Methyl p-hydroxybenzoate | 0.1 g |
| Perfumed composition (essence) | 0.1 g |
| Carboxyvinylpolymer | 1.5 g |
| Triethanolamine | 2 g |
| Depurated water | 61.5 g |

EXAMPLE 7

| Gel | |
|---|---|
| 100 g of gel contain: | |
| 60% eicosapentaenoic acid | 1.0 g |
| Ximeninic acid | 2.5 g |
| Volpo 20 (polyoxyethylene 20 oleylether) | 7.5 g |
| Propylene glycol | 20 g |
| Softigen 767 C$_8$-C$_{12}$ ethoxylated triglycerids) | 20 g |
| Carboxyvinylpolymer | 1.5 g |
| Triethanolamine | 2 g |
| Imidazolidinylurea | 0.3 g |
| Methyl p-hydroxybenzoate | 0.1 g |
| Perfumed composition (essence) | 0.1 g |
| Triethanolamine | 2 g |
| Depurated water | 44 g |

We claim:

1. A method of treating functional or organic peripheral vasculopathies consisting of topically administering to a human subject in need of treatment a pharmaceutical composition containing 0.1 to 10% by weight of an active ingredient which is ximeninic acid or a complex thereof with a phospholipid of formula

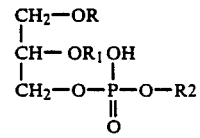

wherein R and R$_1$ are the same or different, and are the acyl residues of palmitic, stearic, oleic, linoleic and linolenic acids, and R$_2$ is the residue of choline, ethanolamine or serine, the phospholipid to ximeninic acid ratio is 0.5 to 2.

2. The method according to claim 1 wherein the phospholipid is soy lecithin.

3. The method according to claim 1 wherein the topically administered pharmaceutical composition is a cream, a gel, a lotion or an ointment.